(12) United States Patent
Kaufman

(10) Patent No.: US 6,228,113 B1
(45) Date of Patent: May 8, 2001

(54) INTRACORNEAL ASTIGMATIC ONLAY

(75) Inventor: Herbert E. Kaufman, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/480,507

(22) Filed: Jan. 10, 2000

(51) Int. Cl.$^7$ .................................................... A61F 2/14
(52) U.S. Cl. ..................... 623/5.11; 623/6.34; 623/6.35
(58) Field of Search .................... 623/5.11, 6.34, 623/6.35

(56) References Cited

U.S. PATENT DOCUMENTS

| | | |
|---|---|---|
| 4,277,852 | 7/1981 | Poler ............................................. 3/13 |
| 4,298,004 | 11/1981 | Schachar et al. ........................ 128/305 |
| 4,435,856 | 3/1984 | L'Esperance .................................. 3/13 |
| 4,512,039 | 4/1985 | Lieberman ...................................... 3/13 |
| 4,585,456 | 4/1986 | Blackmore .................................... 623/6 |
| 4,607,617 | 8/1986 | Choyce ......................................... 128/1 |
| 4,769,035 | 9/1988 | Kelman ........................................ 623/6 |
| 4,816,031 | 3/1989 | Pfoff ............................................ 623/6 |
| 5,123,921 | 6/1992 | Werblin et al. ............................. 623/5 |
| 5,133,747 | 7/1992 | Feaster ........................................ 623/6 |
| 5,171,266 | 12/1992 | Wiley et al. ................................ 623/6 |
| 5,405,384 | 4/1995 | Silvestrini ................................... 623/5 |
| 5,733,334 | 3/1998 | Lee ............................................. 623/5 |
| 5,824,086 | 10/1998 | Silvestrini .................................. 623/5 |
| 5,876,439 | 3/1999 | Lee ............................................. 623/5 |
| 5,888,243 | 3/1999 | Silverstrini ................................. 623/5 |
| 6,138,307 | * 10/2000 | McDonald ............................. 623/5.11 |
| 6,171,336 | * 1/2000 | Sawusch ................................. 623/5.11 |

* cited by examiner

*Primary Examiner*—Dinh X. Nguyen
(74) *Attorney, Agent, or Firm*—Bonnie J. Davis; John H. Runnels

(57) ABSTRACT

An intracorneal astigmatic, rectangular onlay has been discovered that can correct for astigmatism by physically adjusting the shape of the cornea. This astigmatic onlay can be narrow or wide and can easily be placed in the stroma of the cornea. The onlay can be placed on top of a laser ablation or on a spherical lens, which in turn was implanted either under a tissue flap or in a stromal pocket. The astigmatic onlay is easy to position at precisely the correct angle to compensate for the astigmatism-causing meridional distortion. This invention greatly increases the utility and practicality of intracorneal spherical lenses and makes it easy to position the astigmatic correcting ridge at precisely the correct angle to compensate for the astigmatism. The invention greatly decreases the inventory needed to compensate for both spherical and astigmatic corrections. For example, spherical corrections from +5 D to −5 D at 0.25 D intervals might require 40 lenses, but with this invention the addition of a correction for astigmatism up to 5 D at 0.25 D increments would require only 20 additional onlays, for a total of 60 lenses and onlays. By contrast, 800 lenses are required for the same range of corrections if a single lens is used to correct for both astigmatism and spherical errors.

16 Claims, 1 Drawing Sheet

INTRACORNEAL ASTIGMATIC ONLAY

This invention pertain to an optically transparent, intracorneal (intralamellar) onlay that corrects for astigmatism, either alone or in addition to one of various corrections for nearsightedness (myopia) or farsightedness (hyperopia).

In a normal eye, light rays are focused at a single place on the retina, the layer of light-sensitive tissue at the back of the eye. This focusing is accomplished by two structures: first, the cornea, the clear portion at the front of the eye; and second, the natural lens, located inside the eye behind the cornea. The cornea bends (or refracts) the incoming light rays toward a single focal point, providing nearly 80% of the focusing power of the eye. The lens further refines the refraction by directing the light rays onto a precise location on the retina. The retina receives the focused point of light and transmits a signal through the optic nerve to the brain.

Refractive errors, which include nearsightedness, farsightedness, and astigmatism, usually result from a defect in the shape of the cornea in relation to the length of the eye that causes the incoming light to be focused somewhere other than on the retina. In normal vision, the cornea is smooth and the curvature of the cornea is the same in all directions. In persons with nearsightedness or farsightedness (called spherical refractive errors), the curvature of the cornea is either too steep or too flat, respectively. This distortion of the cornea causes the light rays to reach a point of focus either in front or behind the retina, in both cases causing blurred vision.

Spherical refractive errors can be corrected with glasses or contact lenses, and by means of refractive surgery, including radial keratotomy, corneal transplantation, and laser surgery.

Another method for correcting refractive disorders caused by distortion of the cornea is corneal implantation. The cornea has five layers: the outer layer, the epithelium; Bowman's membrane; the multi-layered mid-region, the stroma; a strong membrane layer, Descetmet's membrane; and the inner layer, the endothelium. Corneal implants are usually placed within the multi-layered stroma.

One form of corneal implants to change the curvature of the cornea is a polymeric ring or ring segment (intrastromal corneal ring) or other inserts, placed in the periphery of the cornea (outside the visual field). See, e.g., U.S. Pat. Nos. 5,405,384; 5,733,334; 5,824,086; 5,876,439; and 5,888,243.

U.S. Pat. No. 4,298,004 describes injecting collagen or suitable material into the cornea to alter the radius of curvature.

An intracorneal lens has also been developed to correct for myopia with or without astigmatism. U.S. Pat. No. 5,123,921 describes a circular lens placed in the stroma by cutting a thin slice of tissue from the front of the cornea. The slice remained attached on one side, forming a flap. The flap was lifted, the lens placed on the exposed surface of the stroma, and the flap allowed to fall back over the lens. The refractive properties of the cornea changed because the front surface of the cornea took on the shape of the lens under the flap of tissue. The lens was made of a biocompatible material that allowed metabolites to diffuse easily, ensuring delivery of nutrients necessary for the health of the outer cornea. When correcting for astigmatism, the circular lens was made into a toric lens with different curvatures in different meridians.

U.S. Pat. No. 4,607,617 describes an intracorneal, circular lens made of a polysulfone material of high refractive index placed in the stroma of the cornea to correct refractive defects, which was said also to strengthen and shape the cornea to assist in treating astigmatism.

Astigmatism is another form of refractive error. The curvature of the cornea is warped in one direction. The eye is shaped more like a football than a basketball. This distortion bends incoming light rays in two directions, so that a single focal point is not attained. The multiple focal points result in distorted vision with images appearing indistinct and slanted. Depending on the orientation (or meridian) of the distortion, images are more in focus in one direction than in another. One person with astigmatism may not see vertical lines clearly, another may see fuzzy horizontal lines, and a third may not be able to focus diagonal lines properly. Because this type of refractive error is identified by the axis or meridian in which it is oriented, it may be called a "meridional" error.

Astigmatism can be corrected with glasses or contact lenses, designed to equalize the unequal curvatures of the light caused by the cornea. Because astigmatism is similar to having the spherical cornea bent so that there is a ridge running along one meridian, one approach to correcting astigmatism is to provide a compensating ridge in the orthogonal meridian. Historically, lenses have accomplished this by having different power curves to correct the distortion in different meridians. These lenses are called "toric lenses." Because of the different powers, these lenses have a variable edge profile that is thinner in some places and thicker in others, and are difficult to make.

A variety of approaches to correcting spherical and meridional refractive errors by implanting lenses intraocularly, as contrasted to the intracorneal lens discussed above, have been proposed.

U.S. Pat. No. 4,277,852 describes an intraocular, glass lens that is placed in the eye in front of the natural lens to correct for astigmatism.

U.S. Pat. No. 4,435,856 describes an intraocular, bifocal implant with one lens fixed in the eye for distance and a second lens that can be selectively moved in and out of the optical axis to change the focal length.

U.S. Pat. No. 4,512,039 describes a toric, intraocular lens that corrects postoperative astigmatism by placement in the eye such that the vertical meridian is optically less powerful than the horizontal meridian.

U.S. Pat. No. 4,585,456 describes an intraocular lens that is inlayed on the intact natural lens and a means to maintain the lens position relative to the natural lens.

U.S. Pat. No. 4,769,035 describes an intraocular lens that is implanted on the natural lens to correct for nearsightedness and farsightedness. The circular lens has extensions to help maintain its position on the natural lens.

U.S. Pat. No. 4,816,031 describes an intraocular lens system that includes both a hard lens implant, a soft lens implant, and a microcircuit to change the focal point by varying the distance between the two lenses.

U.S. Pat. No. 5,133,747 describes the adhesion of an artificial, intraocular lens to the natural lens or to a previously implanted lens by adhesives or clips.

U.S. Pat. No. 5,171,266 describes a single intraocular lens that can be adjusted by a surrounding ring to change its power either regularly or more in one meridian than in another to provide astigmatic correction. The surrounding ring is adjusted by changing an external magnetic force.

To make a single lens that corrects for both spherical (nearsightedness and farsightedness) and meridional (astigmatism) visual problems is both mechanically difficult and expensive. Two different power curves are needed to correct astigmatism because the astigmatic cornea splits the light into separate focal points. Also, because of the different powers, the lenses have a variable edge profile, thinner in some parts and thicker in others. Correction of astigmatism in a given individual requires a customized lens to provide the correct spherical and meridional refraction. A large inventory of lenses is needed to encompass a set of combinations of spherical and meridional corrections that will adequately treat most patients. For example, to provide for spherical corrections from +5 diopters (D) to −5 D at 0.25 D intervals, 40 lenses are needed. To also include corrections for astigmatism up to −5 D at 0.25 D increments, a total of 800 lenses would be required.

I have discovered an intracorneal, rectangular onlay, that is a simple correction for astigmatism. This astigmatic onlay can be narrow or wide and can easily be placed in the stroma of the cornea. The onlay can be placed on top of a laser ablation or on a spherical lens, which in turn was implanted either under a tissue flap or in a stromal pocket. The astigmatic onlay is easy to position at precisely the correct angle to compensate for meridional distortion. This invention greatly increases the utility and practicality of intracorneal spherical lenses.

A rectangular astigmatic onlay may be used to correct for astigmatism. This rectangular onlay can be narrow or wide and can be placed on top of a laser ablation (excimer laser tissue removal) or on a spherical lens that is implanted under a tissue flap or in a stromal pocket. The rectangular onlay is permeable to metabolites to maintain the health of the cornea. The rectangular onlay can be oriented to correct for the distorted meridian and need be manufactured only in incremental powers. Thus, spherical corrections from +5 D to −5 D at 0.25 D intervals might require 40 lenses, but with this invention the addition of a correction for astigmatism up to 5 D at 0.25 D increments would require only 20 additional onlays, for a total of 60 lenses and onlays. By contrast, 800 lenses are required for the same range of corrections if a single lens is used to correct for both astigmatism and spherical errors.

The astigmatic, rectangular onlay is preferably made of a material that has a refractive index close to that of the cornea and that is compatible with the tissue of the cornea. Such material may be similar to PERMALENS® (Cooper Vision, Inc., Palo Alto, Calif.) or other similar hydrogel materials as described in U.S. Pat. No. 5,123,921. The rectangular onlay could also have a higher refractive index from that of the cornea, but then the accompanying lens would have to adjust for the additional change in refraction from the rectangular onlay.

As used in the specification and claims, a "rectangular" onlay refers to an onlay that is approximately rectangular when positioned in the cornea and viewed in a direction along the visual axis of the eye. Of course, a "rectangular" onlay will not, in general, be flat in a plane normal to this axis, but will be flexible and will curve to adapt to the curve of the cornea or to the curve of an intracorneal lens. A "rectangular" onlay need not be precisely rectangular when viewed along the visual axis, but must be substantially longer in one direction than in the perpendicular direction. For example, the corners may be rounded, or the onlay may have the shape of an eccentric ellipse, and still be considered "rectangular." The thickness of the onlay in a direction parallel to the visual axis may be varied to accommodate differing degrees of astigmatism, and may be less thick near the edges than in the center.

As used in the specification and claims, the "visual axis" refers to the light path from in front of the eye through the approximate center of the pupil, through the center of the lens, and falling on the fovea of the retina, the spot of greatest visual acuity.

Figure 1B:
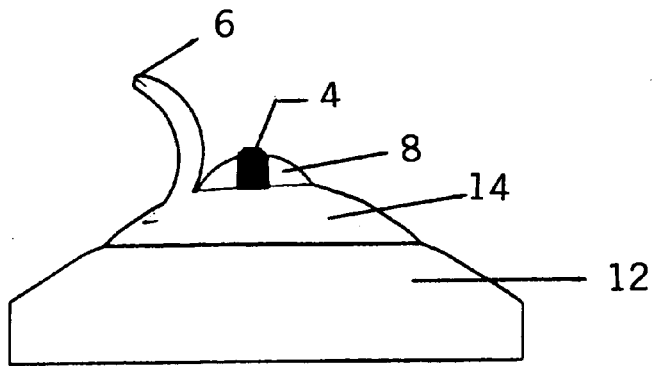
FIG. 1b illustrates a side version of a human eye showing an astigmatic onlay placed in a stromal pocket.
Figure 1A:
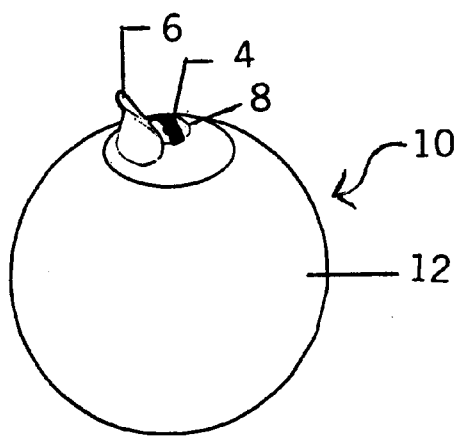
FIG. 1a illustrates a human eye with an astigmatic onlay placed over a spherical lens in a stromal pocket.

The figures illustrate how the intracorneal onlay could be used. FIGS. 1a and 1b illustrate the human eye 10. The outer surface of human eye 10 is covered by the sclera 12, a fibrous outer covering which is primarily white and opaque. At the anterior part of the eye, the sclera 12 becomes the transparent cornea 14. This transparent cornea 14 allows light to enter eye 10. As shown in FIGS. 1a and 1b, an intracorneal lens 8 is implanted into cornea 14.

To implant the intracorneal lens 8, tissue flap 6 is cut by a microkeratome. Tissue flap 6 is lifted, and intracorneal lens 8 is placed on the stroma bed. Astigmatic onlay 4 is then placed on top of intracorneal lens 8 in the astigmatic axis to correct for the meridional distortion of the cornea. Once tissue flap 6 is lowered, the outer surface of the cornea 14 takes on the shape of the implanted lens 8 and onlay 4. The lowered tissue flap will keep the astigmatic onlay 4 and the intracorneal lens 8, if present, in position. The refractive errors of the cornea are thus corrected.

Figure 2:
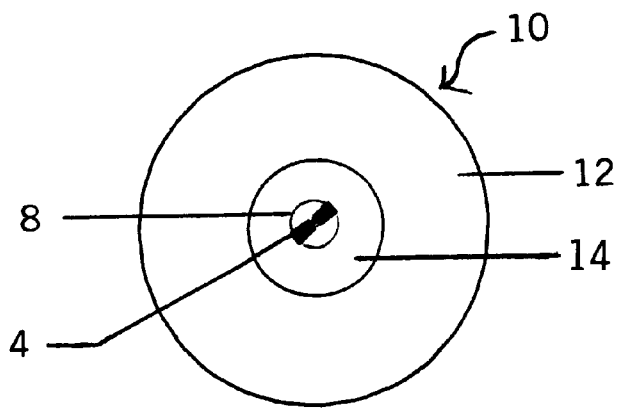
FIG. 2 illustrates a top view of a human eye showing an astigmatic onlay placed in a simple laser ablation.

FIG. 2 illustrates a human eye 10 with an astigmatic onlay 4 placed over an intracorneal lens 8, which has been implanted in a stromal pocket formed by simple dissection. This procedure usually involves cutting a small niche on the side of the cornea and pushing the lens or onlay into place.

The astigmatic onlay can be narrow or wide, depending on the extent of the meridional distortion of the cornea. The dimensions can be determined as needed to correct the corneal curvature for the measured degree of astigmatism. For example, for 5 diopters of astigmatism in a 7 mm optical zone, the thickness of the rectangular onlay required for correction would be approximately 100 microns. The length of the astigmatic onlay is preferably from about 2 mm to about 10 mm; the width, preferably from about 2 to 8 mm; and the thickness, preferably from about 10 to 400 microns. The thickness, however, may decrease toward the edges of the astigmatic onlay.

The complete disclosures of all references cited in this specification are hereby incorporated by reference. In the event of an otherwise irreconcilable conflict, however, the present specification shall control.

I claim:

1. An onlay for correcting astigmatism in a human eye, wherein said onlay is rectangular, wherein said onlay is transparent to visible light, wherein said onlay has a refractive index for visible light that is approximately equal to the refractive index of the human cornea, wherein said onlay is formed of a material that is biocompatible with the human cornea, and wherein said onlay is adapted to correct for a degree of astigmatism by physically changing the shape of the cornea when said onlay is implanted across the visual axis of the cornea of the eye.

2. A combination for correcting both astigmatism and spherical refractive errors in a human eye, said combination comprising an onlay as recited in claim 1 and an intracorneal lens adapted to correct spherical refractive errors when said lens is implanted first into the cornea of the eye.

3. An intracorneal onlay as recited in claim 1, wherein the onlay is adapted to be positioned within the cornea by placement under a tissue flap cut into the cornea.

4. An intracorneal onlay as in claim 1, wherein the onlay is adapted to be positioned within the cornea by placement in a stromal pocket cut into the cornea.

5. A method for correcting astigmatism in a human eye, said method comprising implanting an onlay as recited in claim 1 across the visual axis of the cornea of the eye.

6. A method for correcting both astigmatism and spherical refractive errors in a human eye, said method comprising implanting an onlay as recited in claim 1 and an intracorneal lens adapted to correct spherical refractive errors when said lens is implanted first into the cornea of the eye.

7. A method for correcting astigmatism in a human eye by implanting an onlay as recited in claim 5, wherein the onlay is adapted to be positioned within the cornea by placement under a tissue flap cut into the cornea.

8. A method for correcting astigmatism in a human eye by implanting as onlay as recited in claim 5, wherein the onlay is adapted to be positioned within the cornea by placement in a stromal pocket cut into the cornea.

9. An onlay for correcting astigmatism in a human eye, wherein said onlay is rectangular, wherein said onlay is transparent to visible light, wherein said onlay has a refractive index for visible light that is greater than the refractive index of the human cornea, wherein said onlay is formed of a material that is biocompatible with the human cornea, and wherein said onlay is adapted to correct for a degree of astigmatism by physically changing the shape of the cornea when said onlay is implanted across the visual axis of the cornea of the eye.

10. A combination for correcting both astigmatism and spherical refractive errors in a human eye, said combination comprising an onlay as recited in claim 9 and an intracorneal lens adapted to correct spherical refractive errors when said lens is implanted first into the cornea of the eye.

11. An intracorneal onlay as recited in claim 9, wherein the onlay is adapted to be positioned within the cornea by placement under a tissue flap cut into the cornea.

12. An intracorneal onlay as in claim 9, wherein the onlay is adapted to be positioned within the cornea by placement in a stromal pocket cut into the cornea.

13. A method for correcting astigmatism in a human eye, said method comprising implanting an onlay as recited in claim 9 across the visual axis of the cornea of the eye.

14. A method for correcting both astigmatism and spherical refractive errors in a human eye, said method comprising implanting an onlay as recited in claim 9 and an intracorneal lens adapted to correct spherical refractive errors when said lens is implanted first into the cornea of the eye.

15. A method for correcting astigmatism in a human eye by implanting an onlay as recited in claim 13, wherein the onlay is adapted to be positioned within the cornea by placement under a tissue flap cut into the cornea.

16. A method for correcting astigmatism in a human eye by implanting as onlay as recited in claim 13, wherein the onlay is adapted to be positioned within the cornea by placement in a stromal pocket cut into the cornea.

* * * * *